(12) United States Patent
Houle et al.

(10) Patent No.: US 9,285,362 B2
(45) Date of Patent: Mar. 15, 2016

(54) MEASURING MULTIPLE ANALYTES OVER A BROAD RANGE OF CONCENTRATIONS USING OPTICAL DIFFRACTION

(75) Inventors: Jean-Francois Houle, Toronto (CA); Sriram Kumaraswamy, North York (CA)

(73) Assignee: Axela, Inc., Toronto (CA)

(*) Notice: Subject to any disclaimer, the term of this patent is extended or adjusted under 35 U.S.C. 154(b) by 1877 days.

(21) Appl. No.: 12/445,760

(22) PCT Filed: Oct. 18, 2007

(86) PCT No.: PCT/CA2007/001840
§ 371 (c)(1),
(2), (4) Date: Jan. 6, 2011

(87) PCT Pub. No.: WO2008/046213
PCT Pub. Date: Apr. 24, 2008

(65) Prior Publication Data
US 2011/0091865 A1   Apr. 21, 2011

Related U.S. Application Data

(60) Provisional application No. 60/852,458, filed on Oct. 18, 2006.

(51) Int. Cl.
| G01N 33/543 | (2006.01) |
| G01N 21/03 | (2006.01) |
| G01N 21/47 | (2006.01) |
| G01N 33/68 | (2006.01) |
| G01N 33/72 | (2006.01) |
| G01N 33/74 | (2006.01) |
| G01N 33/78 | (2006.01) |
| G01N 33/92 | (2006.01) |

(52) U.S. Cl.
CPC ...... *G01N 33/54373* (2013.01); *G01N 21/0303* (2013.01); *G01N 21/4788* (2013.01); *G01N 33/6896* (2013.01); *G01N 33/723* (2013.01); *G01N 33/74* (2013.01); *G01N 33/78* (2013.01); *G01N 33/92* (2013.01); *G01N 2800/04* (2013.01); *G01N 2800/042* (2013.01); *G01N 2800/046* (2013.01); *G01N 2800/32* (2013.01)

(58) Field of Classification Search
None
See application file for complete search history.

(56) References Cited

U.S. PATENT DOCUMENTS

| 5,736,343 | A | 4/1998 | Landry |
| 5,795,725 | A | 8/1998 | Buechler et al. |
| 6,156,521 | A | 12/2000 | Buechler et al. |
| 6,174,686 | B1 | 1/2001 | Buechler et al. |
| 6,551,788 | B1 | 4/2003 | Bell |
| 6,991,907 | B1 | 1/2006 | Buechler et al. |
| 6,991,938 | B1 | 1/2006 | Cookson et al. |
| 7,008,794 | B2 | 3/2006 | Goh et al. |
| 7,091,049 | B2 * | 8/2006 | Boga et al. ............ 436/518 |
| 7,098,041 | B2 | 8/2006 | Kaylor et al. |
| 7,102,752 | B2 | 9/2006 | Kaylor et al. |
| 7,118,855 | B2 | 10/2006 | Cohen et al. |
| 7,153,702 | B2 * | 12/2006 | Lin et al. ............ 436/518 |
| 7,169,550 | B2 | 1/2007 | Sayre et al. |
| 7,214,530 | B2 | 5/2007 | Sayre et al. |
| 7,223,368 | B2 | 5/2007 | Cohen et al. |
| 7,223,534 | B2 | 5/2007 | Kaylor et al. |
| 7,244,393 | B2 | 7/2007 | Kaylor et al. |
| 7,314,749 | B2 | 1/2008 | Goh et al. |
| 8,338,189 | B2 | 12/2012 | Lin et al. |
| 2002/0025534 | A1 | 2/2002 | Goh et al. |
| 2003/0049693 | A1 | 3/2003 | Goh et al. |
| 2003/0092092 | A1 | 5/2003 | Pandak et al. |
| 2003/0119209 | A1 * | 6/2003 | Kaylor et al. ............ 436/548 |
| 2005/0112585 | A1 * | 5/2005 | Zichi et al. ............ 435/6 |
| 2005/0227252 | A1 | 10/2005 | Moon et al. |
| 2006/0099649 | A1 * | 5/2006 | Goh et al. ............ 435/7.1 |
| 2006/0264782 | A1 * | 11/2006 | Holmes et al. ............ 600/583 |
| 2007/0154881 | A1 | 7/2007 | Koo |
| 2008/0153109 | A1 | 6/2008 | Eriksson et al. |
| 2011/0111524 | A1 | 5/2011 | Goix et al. |
| 2013/0196338 | A1 | 8/2013 | Lin et al. |

FOREIGN PATENT DOCUMENTS

| JP | 2003/528311 A | 9/2003 |
| JP | 2005502065 A | 1/2005 |
| WO | WO-93/25910 A1 | 12/1993 |
| WO | WO-97/26534 A1 | 7/1997 |
| WO | WO-01/71322 A2 | 9/2001 |
| WO | WO-03/023400 A2 | 3/2003 |
| WO | WO-2005/050207 A2 | 6/2005 |
| WO | WO-2005/061237 A1 | 7/2005 |
| WO | WO-2005/062021 A1 | 7/2005 |

OTHER PUBLICATIONS

Wild, The Immunoassay Handbook, Stockton Press, 1994, p. 66.*

Altwegg et al., "Myeloid-related protein 8/14 complex is released by monocytes and granulocytes at the site of coronary occlusion: a novel, early, and sensitive marker of acute coronary syndromes," Eur Heart J. 28(8):941-948 (2007).

Borisenko et al., "Diffractive optics technology: a novel detection technology for immunoassays," Clin Chem. 52(11):2168-2170 (2006).

(Continued)

*Primary Examiner* — Gary W Counts
(74) *Attorney, Agent, or Firm* — Clark & Elbing LLP

(57) ABSTRACT

Methods, devices, and kits for measuring multiple analytes in a sample having a broad range of concentrations using optical diffraction are disclosed. Devices, methods, and kits useful for monitoring and diagnosing diabetes, cardiovascular disease, thyroid disease, hormone-related conditions, and sepsis are also described.

55 Claims, 11 Drawing Sheets

(56) References Cited

OTHER PUBLICATIONS

Cao et al., "Double-enhancement strategy: A practical approach to a femto-molar level detection of prostate specific antigen-alpha1-antichymotrypsin (PSA/ACT) complex for SPR immunosensing," J Microbiol Biotechnol. 17(6):1031-1035 (2007).

Dahl et al., "Plasma concentration of Gc-globulin is associated with organ dysfunction and sepsis after injury," Crit Care Med. 31(1):152-156 (2003).

Goh et al. "A quantitative diffraction-based sandwich immunoassay," Anal Biochem. 313(2):262-266 (2003).

Goh et al., "Diffraction-based assay for detecting multiple analytes," Anal Bioanal Chem. 374(1):54-56 (2002).

HyTest Ltd., "Markers of cardiovascular diseases and metabolic syndrome," <http://www.hytest.fi/catalogs>, retrieved Jun. 6, 2012 (108 pages).

Lee et al., "Relative value of multiple plasma biomarkers as risk factors for coronary artery disease and death in an angiography cohort," CMAJ. 174(4):461-466 (2006).

Lin et al., "Development of a novel diffraction-based immunoassay for characterizing the primary and ternary structure of the circulating form of cardiac troponin," Poster presented on Jan. 29, 2010 (7 pages).

Lin et al., "Development of a qualitative sequential immunoassay for characterizing the intrinsic properties of circulating cardiac troponin I," Clin Chem. 56(8):1307-1319 (2010).

Lin et al., "Intra-feature and inter-feature multiplexing using diffractive optics technology: more information from less sample," Poster presented at the 41st annual Oak Ridge Conference, Baltimore, MD, Apr. 16 & 17, 2009 (1 page).

Loo et al., "An enzyme-amplified diffraction-based immunoassay," Anal Biochem. 337(2):338-342 (2005).

Meisner, "Biomarkers of sepsis: clinically useful?," Curr Opin Crit Care. 11(5):473-480 (2005).

Morgenthaler et al., "Assay for the measurement of copeptin, a stable peptide derived from the precursor of vasopressin," Clin Chem. 52(1):112-119 (2006).

Morjana, "Degradation of human cardiac troponin I after myocardial infarction," Biotechnol Appl Biochem. 28(Pt 2):105-111 (1998).

Ndao et al., "Rapid determination of Strongyloides infection using a novel diffractive optics technology," Poster presented on Sep. 26, 2009 (1 page).

Pearson et al., "Switching from insulin to oral sulfonylureas in patients with diabetes due to Kir6.2 mutations," N Engl J Med. 355(5):467-477 (2006).

International Search Report and Written Opinion for International Application No. PCT/CA2007/001840, mailed Feb. 4, 2008 (18 pages).

Communication enclosing the Supplementary European Search Report for European Application No. 07815991.0, dated Feb. 16, 2010 (13 pages).

Communication enclosing the Partial European Search Report for European Application No. 12004386.4, dated Dec. 3, 2012 (8 pages).

Communication enclosing the Extended European Search Report for European Application No. 12004386.4 dated Mar. 25, 2013 (13 pages).

\* cited by examiner

| Disease indication | Concentration range | | | |
|---|---|---|---|---|
| | mMol | μMol | nMol | pMol |
| Cardiovascular Risk | HDL, LDL | CRP | SAA | IL-6, NT-proBNP |
| Diabetes Management | Hb1Ac | Apolipo-proteins | Complement | C-peptide, insulin |
| Sepsis | | CRP, Gelsolin | | Copeptin Cytokines |
| Thyroid function | | Anti-TPO Abs | | TSH |

FIG. 8

MEASURING MULTIPLE ANALYTES OVER A BROAD RANGE OF CONCENTRATIONS USING OPTICAL DIFFRACTION

CROSS-REFERENCE TO RELATED APPLICATIONS

This application is the U.S. National Stage of PCT/CA2007/001840, filed Oct. 18, 2007, which claims benefit of U.S. Provisional Application No. 60/852,458, filed Oct. 18, 2006, which is hereby incorporated by reference.

BACKGROUND OF THE INVENTION

The invention relates to the fields of optical diffraction and analyte detection.

In many clinical settings the proper assessment of a patient's symptoms requires the determination and quantification of multiple analytes over a broad dynamic range. Detection technologies relying on light emission from labels often suffer from crosstalk where a strong signal originating from the binding of one analyte may drown out weaker signals. Some assay developers dilute the sample to lower the signal of the high concentration analyte, but this solution is limited in its ability to extend dynamic range as the dilution may ultimately hinder the ability to measure the analytes having lower concentrations.

In order to counter these issues, some have developed fluorophores with very distinct spectral properties, e.g., quantum dots, which must be analyzed using different excitation and emission filters. Others, such as described in U.S. Pat. No. 6,551,788, have relied on particle size differences to distinguish and quantify several analytes in one sample, adding the difficult step of controlling particle size so that analytes can be distinguished.

Other technologies such as capillary electrophoresis use a single label to resolve individual antibody-antigen complexes. All of these approaches rely heavily on cumbersome methods that may limit their application in cost-sensitive or rugged environments.

There is a need for new methods of detecting multiple analytes over a broad concentration range.

SUMMARY OF THE INVENTION

The invention relates to method, devices, and kits for measuring multiple analytes in a sample having a broad range of concentrations using optical diffraction. Devices, methods, and kits useful for monitoring and diagnosing diabetes, cardiovascular disease, thyroid disease, hormone-related conditions, and sepsis are also described.

The invention features a method of detecting, in parallel, analytes in a sample, wherein the concentration of a first analyte is at least 100 times greater than the concentration of a second analyte, including contacting the sample with a device having a first immobilized binding agent to which the first analyte specifically binds and a second immobilized binding agent to which the second analyte specifically binds, wherein each of the binding agents is disposed in a pattern capable of optical diffraction when the first or second analyte binds thereto, and measuring the optical diffraction from each of the patterns to detect the presence or absence of the first and second analytes. The method may additionally include determining the concentration of analyte in the sample or calculating the rate of binding or a binding constant of the first or second analyte to the first or second binding agent. The analytes assayed by the method include, e.g., DNA, RNA, protein, or lipid or may be a virion or a cell. The method may measure direct binding of an analyte to a binding agent or indirectly measure binding of an analyte using an additional moiety to amplify the optical diffraction. Examples of additional moieties include enzymes such as horseradish peroxidase and alkaline phosphatase or a bead. Enzymes may amplify optical diffraction by acting on a substrate to cause precipitation of the substrate or binding of the substrate to the enzyme, binding agent, or target. The concentrations of analytes in a sample employed by the method may differ by a factor of at least 1,000, 10,000, 100,000, 1,000,000, 10,000,000, 100,000,000, or 1,000,000,000. The concentrations of analytes in a sample employed by the method may be less than 100 milligrams/milliliter, 10 milligrams/milliliter, 1 milligram/milliliter, 100 micrograms/milliliter, 10 micrograms/milliliter, 1 microgram/milliliter, 100 nanograms/milliliter, 10 nanograms/milliliter, 1 nanogram/milliliter, 100 picograms/milliliter, 10 picograms/milliliter, or 1 picogram/milliliter. The binding agents may contain, e.g., a protein, e.g., an antibody, or a polynucleotide. The binding agents may also be immobilized, e.g., via a biotin-avidin or biotin-streptavidin interaction, Protein G, Goat Anti-Mouse-Fc (GAM-Fc), or an amide bond. The method may employ a device having a third or a fourth binding agent that selectively binds a third or fourth analyte and measures the binding of the third or fourth analyte. Exemplary analytes include C-peptide, glycated hemoglobin, a lipoprotein, a low-density lipoprotein (LDL), a high-density lipoprotein (HDL), a cytokine, IL-6, thyroid stimulating hormone (TSH), anti-thyroid peroxidase (TPO) antibody, a hormone, CRP, NT-proBNP, gelsolin, or copeptin.

The invention also features a device having a first immobilized binding agent that specifically binds C-peptide and a second immobilized binding agent that specifically binds glycated hemoglobin, wherein each of the binding agents is disposed in a pattern capable of optical diffraction when C-peptide or glycated hemoglobin binds thereto. In a further embodiment, the invention also includes a kit for diagnosing diabetes using this device and an additional moiety capable of amplifying the optical diffraction caused by binding of C-peptide or glycated hemoglobin.

The invention further features a device having a first immobilized binding agent that specifically binds a first analyte selected from the group consisting of lipoproteins, low-density lipids (LDL), high-density lipids (HDL), cytokines, and IL-6 and a second different immobilized binding agent that specifically binds a second analyte from the group consisting of lipoproteins, low-density lipids (LDL), high-density lipids (HDL), cytokines, and IL-6, wherein each of the binding agents is disposed in a pattern capable of optical diffraction when the first or second analyte binds thereto. In a further embodiment, this invention features a kit for diagnosing a cardiovascular disease using this device and an additional moiety capable of amplifying the optical diffraction caused by binding of first or second analyte.

In another aspect, the invention features a device having a first immobilized binding agent that specifically binds TSH and a second immobilized binding agent that specifically binds anti-TPO antibody, wherein each of the binding agents is disposed in a pattern capable of optical diffraction when TSH or anti-TPO antibody binds thereto. In a further embodiment, the invention features a kit for diagnosing a thyroid disease using this device and an additional moiety capable of amplifying the optical diffraction caused by binding of TSH or anti-TPO antibody.

The invention features a device having a first immobilized binding agent that specifically binds a hormone and a second immobilized binding agent that specifically binds a different hormone, wherein each of the binding agents is disposed in a pattern capable of optical diffraction when the first or second hormone binds thereto. In a further embodiment, the invention features a kit using this device and an additional moiety capable of amplifying the optical diffraction caused by binding of the first or second hormone.

The invention also features a device having a first immobilized binding agent that specifically binds a first analyte selected from the group consisting of cytokines, CRP, gelsolin, and copeptin and a second different immobilized binding agent that specifically binds a second analyte from the group consisting of cytokines, CRP, gelsolin, and copeptin, wherein each of the binding agents is disposed in a pattern capable of optical diffraction when the first or second analyte binds thereto. In a further embodiment, the invention features a kit for diagnosing sepsis using this device and an additional moiety capable of amplifying the optical diffraction caused by binding of the first or second analyte.

The invention also features a device having a first immobilized binding agent that specifically binds CRP and a second different immobilized binding agent that specifically binds NT-proBNP, wherein each of the binding agents is disposed in a pattern capable of optical diffraction when the CRP or NT-proBNP binds thereto. In a further embodiment, the invention features a kit for diagnosing a condition, e.g., cardiovascular disease, using this device and an additional moiety capable of amplifying the optical diffraction caused by binding of NT-proBNP. Devices and kits of the invention may also detect NT-proBNP and one or more markers of cardiovascular disease.

By "additional moiety" is meant any substance, compound, or molecule that participates in a complex containing other substances, compounds, or molecules, e.g., a complex containing the additional moiety, a binding agent, and an analyte. The additional moiety may enhance the optical diffraction induced by the binding of the analyte to the binding agent by inducing precipitation of enzyme substrates onto or binding to the analyte and thereby providing a greater amount of material deposited on the diffraction pattern that can amplify the optical diffraction.

By "analyte" is meant a molecule, other chemical species, e.g., an ion, or particle. Exemplary analytes include cells, viruses, nucleic acids, proteins, carbohydrates, and small organic molecules.

By "binding agent" is meant any substance, compound, or molecule to which an analyte binds. A binding agent may be coupled to a surface to which an analyte binds or be part of the material making up the surface to which an analyte binds. Exemplary binding agents include antibodies, oligo- or polypeptides, nucleic acids, other proteins, synthetic polymers, and carbohydrates.

By "measuring direct binding" is meant measuring binding of an analyte to a binding agent without use of an additional moiety.

By "measuring binding indirectly" is meant measuring binding of an analyte to a binding agent with the use of an additional moiety.

Other features and advantages of the invention will be apparent from the following Detailed Description, the drawings, and the claims.

BRIEF DESCRIPTION OF THE DRAWINGS

FIG. 8 shows a table describing the use of the invention to measure multiple analytes having concentrations ranging from millimolar to picomolar to assess and diagnose various diseases.

DETAILED DESCRIPTION OF THE INVENTION

Figure 1:
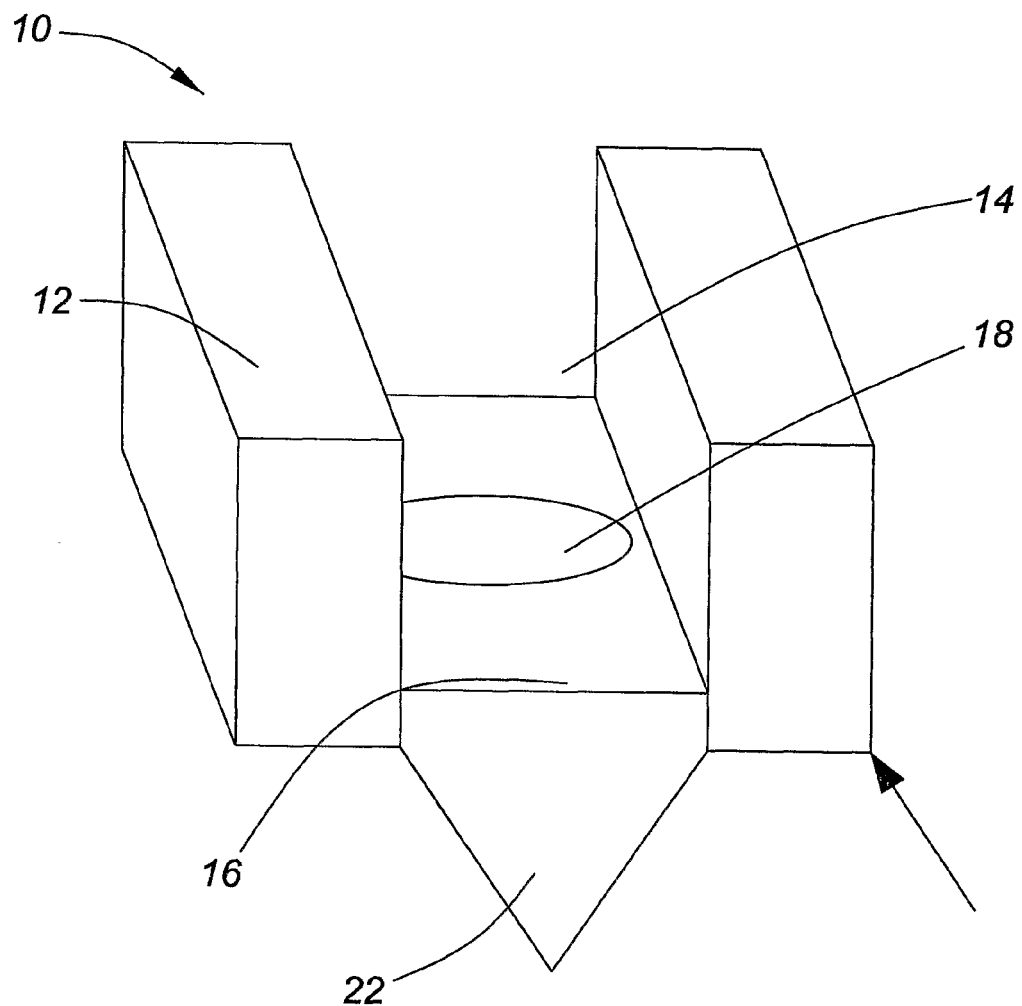
FIG. 1 is a perspective view of a disposable reaction vessel with an integrated optical element having an analyte-specific pattern in a single reaction chamber with a prism integrally formed with the bottom of the reaction chamber.

The invention provides devices, methods, and kits for measuring, in parallel, multiple analytes in a sample that have disparate concentrations, e.g., ranging from millimolar to picomolar. We have demonstrated the parallel measurement of two analytes in a single sample present at concentrations differing by a factor of more than one million. The invention also provides kits and devices that can be used to assess the presence of various biomarkers in a sample from a subject to facilitate diagnoses of disease and clinical assessments.

Methods of Measuring Multiple Analytes

The methods of the invention employ two technologies: grating-based light diffraction and immobilized capture surfaces. This combination produces a sensitive and very simple technique for the detection of molecular binding events without the use of fluorescent labels.

The method of the invention detects, in parallel, analytes in a sample, wherein the concentration of a first analyte is at least 100 times greater than the concentration of a second analyte, by contacting the sample with a device having a first immobilized binding agent to which the first analyte specifically binds and a second immobilized binding agent to which the second analyte specifically binds. Each of the binding agents is disposed in a pattern capable of optical diffraction when the first or second analyte binds thereto. Measurement of the optical diffraction from each of the patterns is used to detect the presence or absence of the first and second analytes. The concentration of analyte in the sample may be determined using this measurement of optical diffraction. Furthermore, rate of binding or a binding constant of one of the analytes to one of the binding agents may be calculated.

Using an exemplary device, the method may employ protein-specific binding agents, which are immobilized on the device surface in eight distinct locations or assay spots. The binding agents within each spot are not randomly distributed, but are immobilized in a series of parallel lines that produces a specific diffraction pattern when illuminated with a laser. The sensor surface forms the base of a low-volume flow cell. When a sample is introduced into the flow cell, e.g., as a flowing stream or a static volume, target molecules bind to the assay spots, resulting in an increased diffraction signal. The intensity of the diffraction signal is used to generate real-time binding curves. The illumination and detection beams never pass through the sample, which makes the invention ideal for the detection of multiple proteins in complex biological samples such as serum, plasma, and crude cell lysates.

Various analytes in a sample can be analyzed by the method of the invention, e.g., DNA, RNA, protein, or lipid or an entire virion or cell. Preferred analytes include C-peptide, glycated hemoglobin, a lipoprotein, a low-density lipoprotein (LDL), a high-density lipoprotein (HDL), a cytokine, IL-6, TSH, anti-TPO antibody, a hormone, CRP, NT-proBNP, gelsolin, or copeptin. Various concentrations of multiple analytes can be measured in parallel, e.g., measuring analytes with concentrations less than 100 milligrams/milliliter, 10 milligrams/milliliter, 1 milligram/milliliter, 100 micrograms/milliliter, 10 micrograms/milliliter, 1 microgram/milliliter, 100 nanograms/milliliter, 10 nanograms/milliliter, 1 nanogram/milliliter, 100 picograms/milliliter, 10 picograms/milliliter, or 1 picogram/milliliter. The concentration of the analytes detected may differ by a factor of 100, 1,000, 10,000, 100,000, 1,000,000, 10,000,000, 100,000,000, or 1,000,000,000.

Various binding agents may be employed by the methods of the invention including proteins, e.g., an antibody, or polynucleotides. These binding agents may be immobilized by a biotin avidin or biotin streptavidin interaction, Protein G, Goat Anti-Mouse-Fc (GAM-Fc), or an amide bond.

The optical diffraction signals of analytes being measured may be measured directly (measuring direct binding without amplification by additional moieties) or indirectly by using additional moieties to amplify the signal. The optical diffraction signal may be amplified using additional moieties such as enzymes like horseradish peroxidase or alkaline phosphatase or beads, e.g., conjugated to antibodies or other binding agents that bind to an analyte, possible via an epitope that differs from that that binds the analyte to the surface.

The method can also be scaled to measure two, three, four, or more analytes in a sample simultaneously using devices having two, three, four, or more binding agents.

Methods for using the optical diffraction-based devices in diffraction-based assay will be known to those skilled in the art based on pertinent patents and literature references such as in Goh et al., "Diffraction-Based Assay for Detecting Multiple Analytes" Anal. Bioanal. Chem (2002) 374, 54-56, which is incorporated by reference.

Analytes

Any number of different analytes may be detected by the invention. Exemplary analytes include biomarkers and biomolecules, e.g., DNA, RNA, microRNA, polynucleotides and their homologues, proteins, or lipids, as well as larger assemblies, such as virions or whole cells. Of particular interest are biomarkers including, e.g., C-peptide, glycated hemoglobin, lipoproteins, low-density lipoprotein (LDL), high-density lipoprotein (HDL), cytokines, IL-6, TSH, anti-TPO antibody, hormone, C-Reactive Protein (CRP), gelsolin, and copeptin.

Uses of the Invention

Both direct and amplified (indirect) detection methods can be used with the invention's devices, kits, and methods, enabling quantitative measurement of multiple analytes in parallel across a broad dynamic range—from picomolar to millimolar concentrations. Typically, detection of one analyte will be direct, while detection of another analyte will be indirect. Because method development is accelerated, assay implementation and assay transfer to and from the platform is more straightforward.

Spanning assay development to biomarker detection, the invention contributes to each stage of the assay development process. Extrapolation from end-point results is eliminated, as the invention generates real-time binding data. The invention speeds assay development in numerous ways including, e.g., quantifying reagent concentration and purity, ranking antibody affinity, characterizing antibody binding kinetics, determining antibody specificity and cross-reactivity, optimizing reagent concentrations, step times, buffers, and additive composition, monitoring assay performance and matrix effects, and multiplexing analytes with minimized interference.

The invention also permits a wide range of additional applications including, e.g., aggregation studies, substrate/activity measurements, enzyme inhibition studies, monitoring levels of biomarkers (with and without disease relevance), and the detection of large species such as viral particles, microorganisms and cells.

Diffraction is inherently self-referencing—since the detection of binding events is dependent on the initial pattern of binding agents, an increase in signal occurs only when analytes bind exclusively to those binding agents. Non-specific binding to the surface of the devices employed by the invention generally produces little or no change in the diffraction signal. This label-free characteristic of the invention enables the direct study of multiple biomolecular interactions in parallel including, e.g., protein-protein interactions, nucleic acid interactions, and nucleic acid-protein interactions.

The methods of the invention may be used to monitor patients and diagnose disease. In diabetes management, physicians and researchers may use the invention to monitor, in parallel, C-peptide levels in the pMol range and glycated hemoglobin levels that can reach up to 8% of the 7.4-11.2 mmol/L of the total hemoglobin found in blood (NEJM 355; 5:467-477) (FIG. 8). Such information may be employed for diagnosis, prognosis, and response to therapy.

Similarly, physicians and researchers may use the invention to monitor plasma biomarkers such as lipoproteins, e.g., LDL and HDL, which can reach mmol levels while other markers such as cytokines, e.g., IL-6, are found in ng/L concentrations, essentially pMol (CMAJ 174; 4:461-466) in order to assess cardiovascular disease in a subject (FIG. 8).

Alternatively, physicians and researchers may use the invention to monitor in parallel thyroid function by determining the amount of TSH, which typically requires a highly sensitive immunoassay, and the detection of anti-TPO antibodies that are typically several orders of magnitude larger than TSH levels in order to assess thyroid disease in a subject (FIG. 8).

Physicians and researchers may also use the invention to monitor in parallel multiple hormones to assess various physical conditions, such as pregnancy, ovulation, menopause, and diseases such as cancer.

Physicians and researchers may also use the invention to monitor in parallel various cytokines, which are initially detected at picomolar levels, and other biomarkers such as CRP are in the mg/L range (Curr Op Crit Care 11:473-480) in order to assess sepsis in a subject. Other markers that may be monitored in parallel by the invention include, e.g., gelsolin (Crit Car Med 31:152-156) and copeptin (Clin Chem; 51:1: 112-119), which span the concentration continuum from mg/L to pMol in order to assess sepsis in a subject (FIG. 8). NT-proBNP in serum is generally in the pMol range.

Optical Diffraction-Based Devices and their Fabrication

A number of exemplary devices may be employed by the invention. For example, a device having a single reaction chamber with integral prism is useful for compact devices requiring assay of one or two analytes. FIG. 1 shows such a device having a disposable reaction vessel 10 with integrated optical element. Reaction vessel 10 includes a housing 12 enclosing a well or chamber 14. Housing 12 has an inner bottom surface 16 on which a pre-selected pattern 18 of analyte binding agents is formed for detecting any number of analytes. On an outer bottom surface 20 of housing 12 is a prism 22, which is integrally formed with the rest of housing 12. The housing 12 with integrated prism 22 may be produced of any suitable plastic, generally a clear transparent plastic at the wavelengths to be used to illuminate the pattern through the prism 22.

Figure 2:
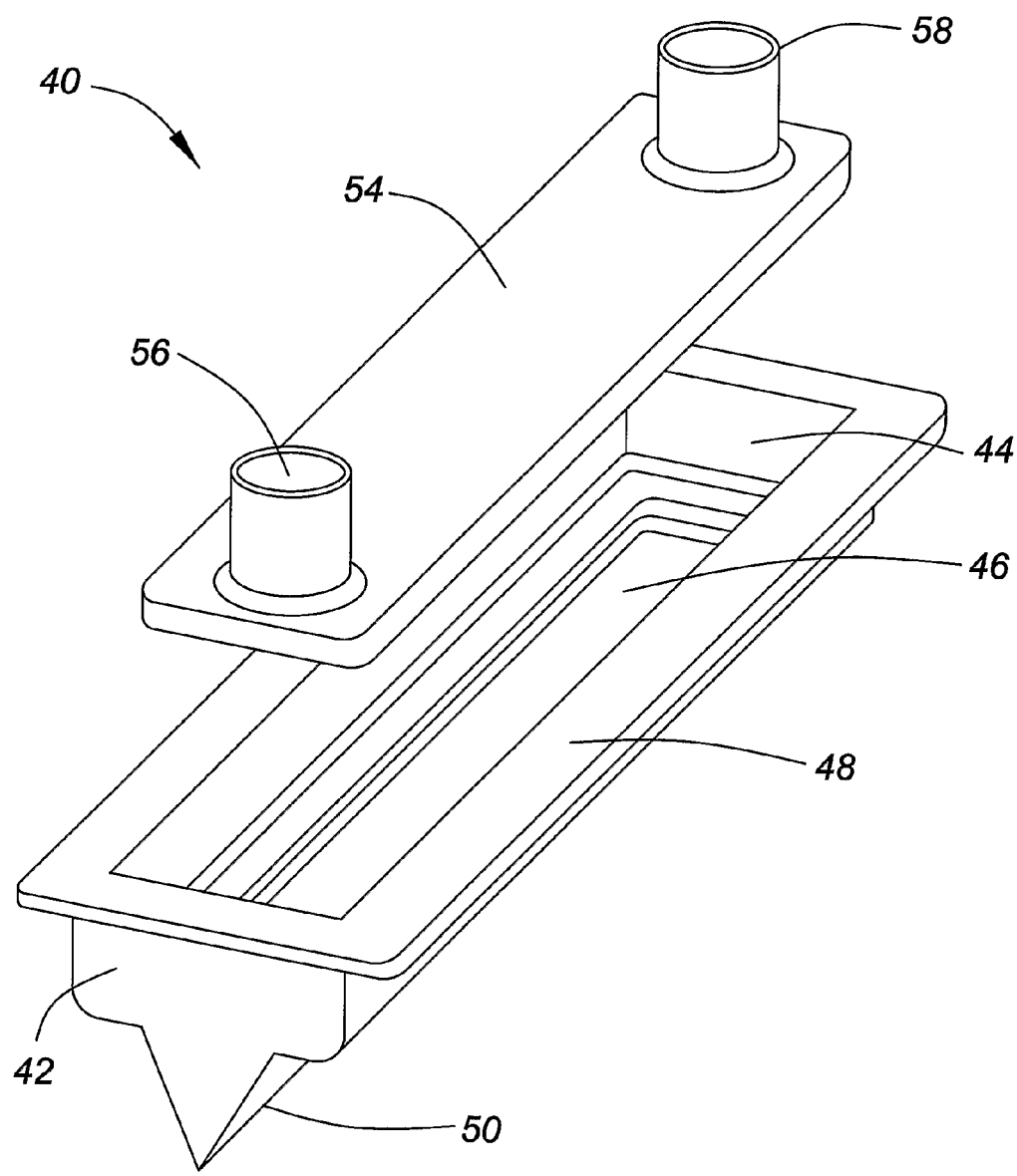
FIG. 2 is a perspective view of another embodiment of a disposable reaction vessel having an elongated reaction chamber with a linear array of analyte-specific patterns along the bottom of the reaction chamber with an elongated prism integrally formed along the bottom of the housing containing the reaction chamber.

For multiple assay formats using multiple analyte specific binding agents but one reaction chamber, the present invention may employ, e.g., a disposable reaction vessel 40 shown in FIG. 2, which includes a housing portion 42 enclosing a well or chamber 44, with the housing having an inner bottom surface 46 along which a linear array of analyte specific binding agents 48 are formed with an elongated single prism 50 integrally formed along the bottom outer surface of housing 42 thus giving a single consumable with an elongated prism. Disposable reaction vessel 40 includes a housing cover 54 having a fluid inlet 56 and a fluid outlet 58.

When housing 42 is assembled with cover 54, fluid containing the analyte to be analyzed may be flowed through inlet 56 and out through outlet 58.

In one exemplary device, when cover 54 is assembled with housing 42, the volume of interior chamber 44 is such that a capillary flow path is formed through the chamber between the inlet 56 and outlet 58. This device contains a disposable reaction vessel 40 with integrated optical elements is appropriate for situations where a compact consumable is desired and up to approximately thirty (30) discrete assays of binding agents are required.

Other devices that may be employed by the current invention have been described in International Applications WO 2005/061237 and WO 2005/062021 and U.S. Patent Application 2002/0025534 and 2003/0049693, each of which is hereby incorporated by reference.

Surfaces and Binding Agents

The invention uses sensors, e.g., flow-through sensors, for the detection of biomolecular binding events between binding agents and analytes. Several optimized binding surfaces are available to address a broad range of applications. The disposable design of the invention's devices make them ideal for the analysis of multiple components of complex biological samples.

Avidin-Coated Surface and Immobilized Binding Agents

Immobilized avidin groups on the sensor surface are used for high-affinity immobilization of biotinylated binding agents, e.g., biotinylated antibodies or polynucleotides, on the surfaces of the devices employed by the invention.

Protein G-Coated Surface and Immobilized Binding Agents

Protein G selectively binds to the Fc region of human and rabbit immunoglobulin molecules, allowing oriented immobilization of human and rabbit antibodies, as binding agents, on the surfaces of the devices employed by the invention.

Goat Anti-Mouse-Fc (GAM-Fc)-Coated Surface and Immobilized Binding Agents

GAM-Fc efficiently binds to the Fc region of mouse antibodies, allowing oriented immobilization of binding agents, e.g., mouse antibodies on the surfaces of the devices employed by the invention. The GAM-Fc surface is suitable for antibody characterization studies and immunoassay applications.

Amine-Reactive Surface and Immobilized binding Agents.

Immobilized carboxylate groups on the amine-reactive surface can be used to covalently link binding agents, with amide bonds for example, to the surface of the devices employed by the invention via an amine coupling reaction. Proteins, peptides, nucleic acids, and other biomolecules can be immobilized.

Miscellaneous

Other exemplary reactive linking groups such as hydrazines, hydroxylamines, thiols, carboxylic acids, epoxides, trialkoxysilanes, dialkoxysilanes, and chlorosilanes may be attached to the surface of the devices employed by the invention such that binding agents may form chemical bonds with those linking groups to immobilize them on the surface of the device.

Various exemplary surfaces used in the devices employed by the invention include polystyrene, glass, metal, silicon, and other semiconductors. Surfaces used in devices employed by the invention may include any substance capable of immobilizing binding agents.

Exemplary binding agents used in the devices employed by the invention may be molecules, e.g., antibodies, polynucleotides, enzymes, receptors, ligands, or molecules with molecular weights below 500, which can be immobilized on the surface of a device employed by the invention. Binding agents used in the invention include any substance capable of binding an analyte.

Other exemplary binding agents used in the devices employed by the invention may be, e.g., magnetic, positively charged, negatively charged, polarized, or capable of forming temporary dipoles, so that the binding agents may bind analytes in a sample by non-covalent means.

EXAMPLE

Example 1

Two Spot Dynamic Range Assay

Figure 3:
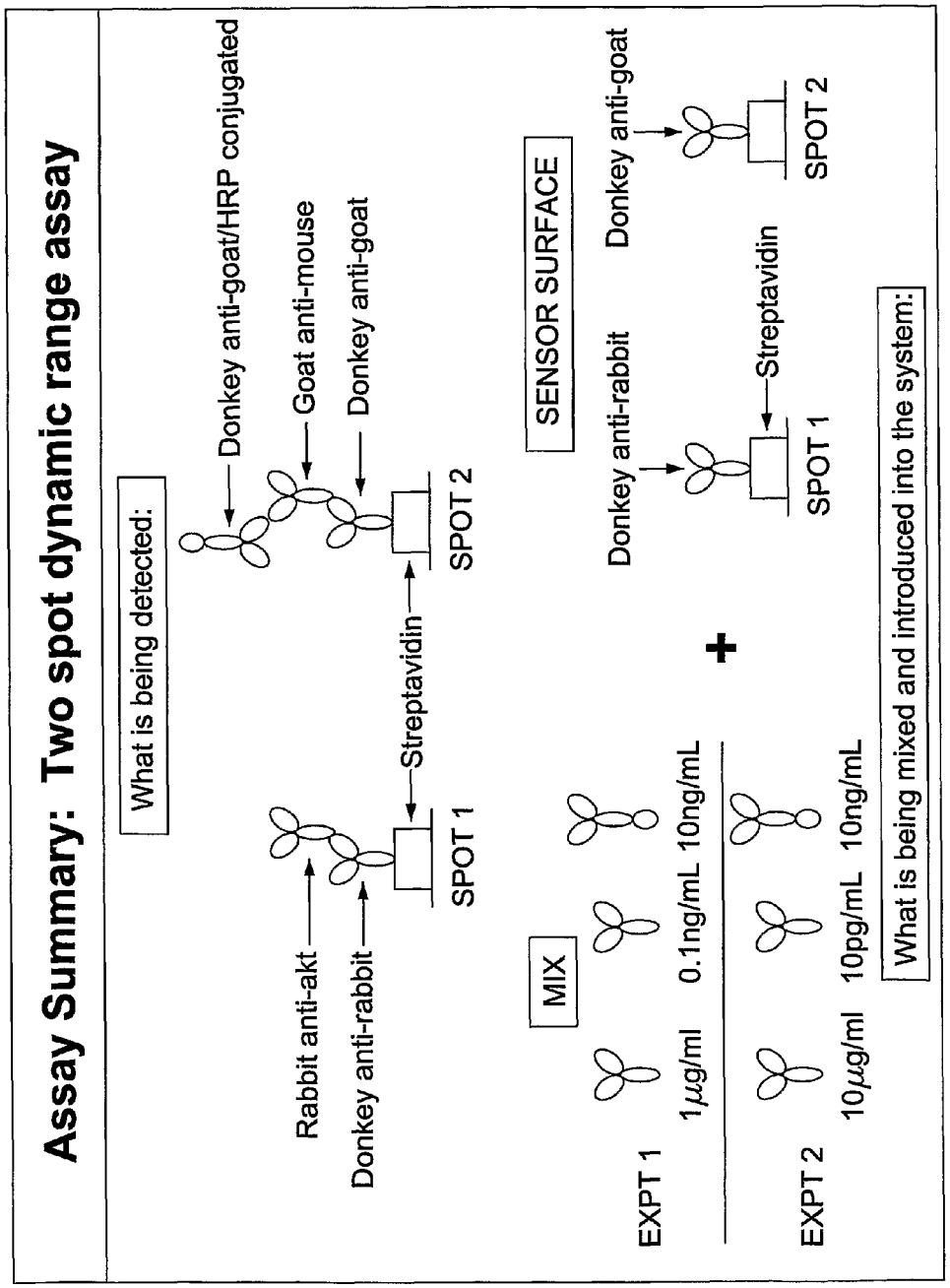
FIG. 3 is a schematic of a two spot sensor and dynamic range assay. SPOT 1 contains a donkey anti-rabbit antibody as a binding agent and SPOT 2 contains a donkey anti-goat antibody as a binding agent. Both of the binding agents are biotinylated and adhere to a streptavidin-coated surface. The signal on SPOT 2 will be enhanced by TMB (3,3',5,5'-tetramethylbenzidine) precipitation using a horseradish peroxidase-conjugated antibody.

We utilized a streptavidin coated diffractive optical sensor (DOT™, Axela Biosciences) which was spotted in two separate locations with 1) a biotinylated Donkey anti-rabbit antibody (SPOT 1) and 2) a biotinylated Donkey anti goat antibody (SPOT2) (FIG. 3). We premixed three components: A) a rabbit anti-akt antibody that will serve as the target analyte for the donkey anti-rabbit on SPOT1 B) a goat anti-mouse antibody which will serve as the target analyte for SPOT2 as well as C) a donkey anti-goat antibody coupled to Horseradish Peroxidase which will serve to enhance the signal obtained from analyte binding to SPOT2.

Figure 4:
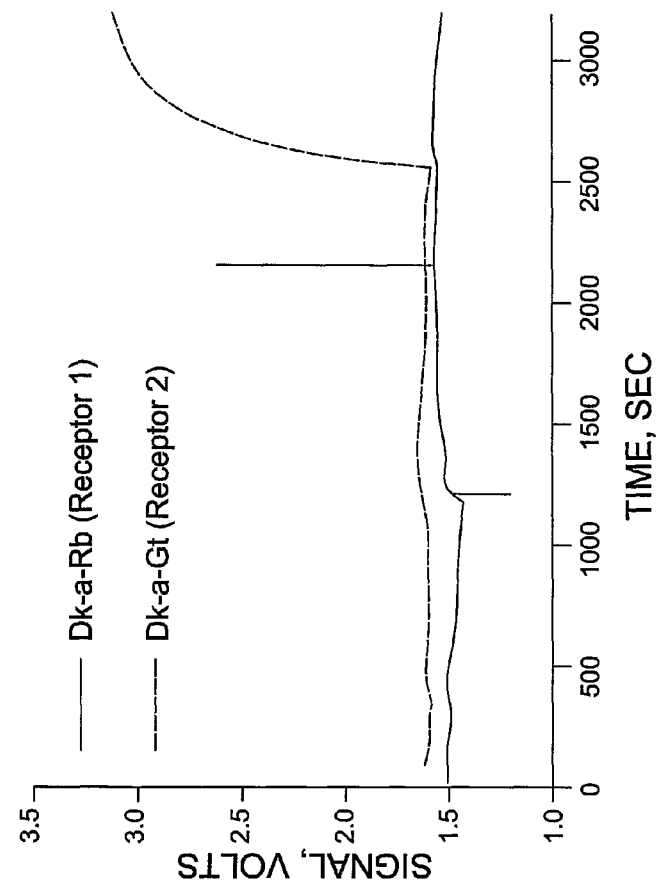
FIG. 4 shows the detection of two analytes binding over a 10,000-fold concentration range. The signals (in volts) induced by the dynamic range assay portrayed in FIG. 3 of Rabbit anti-Akt (Rbα.Akt) (1 µg/mL) and Goat anti-mouse (Gtα.Ms) (0.1 ng/mL) binding to their substrates are shown as a function of time (in seconds).
Figure 5:
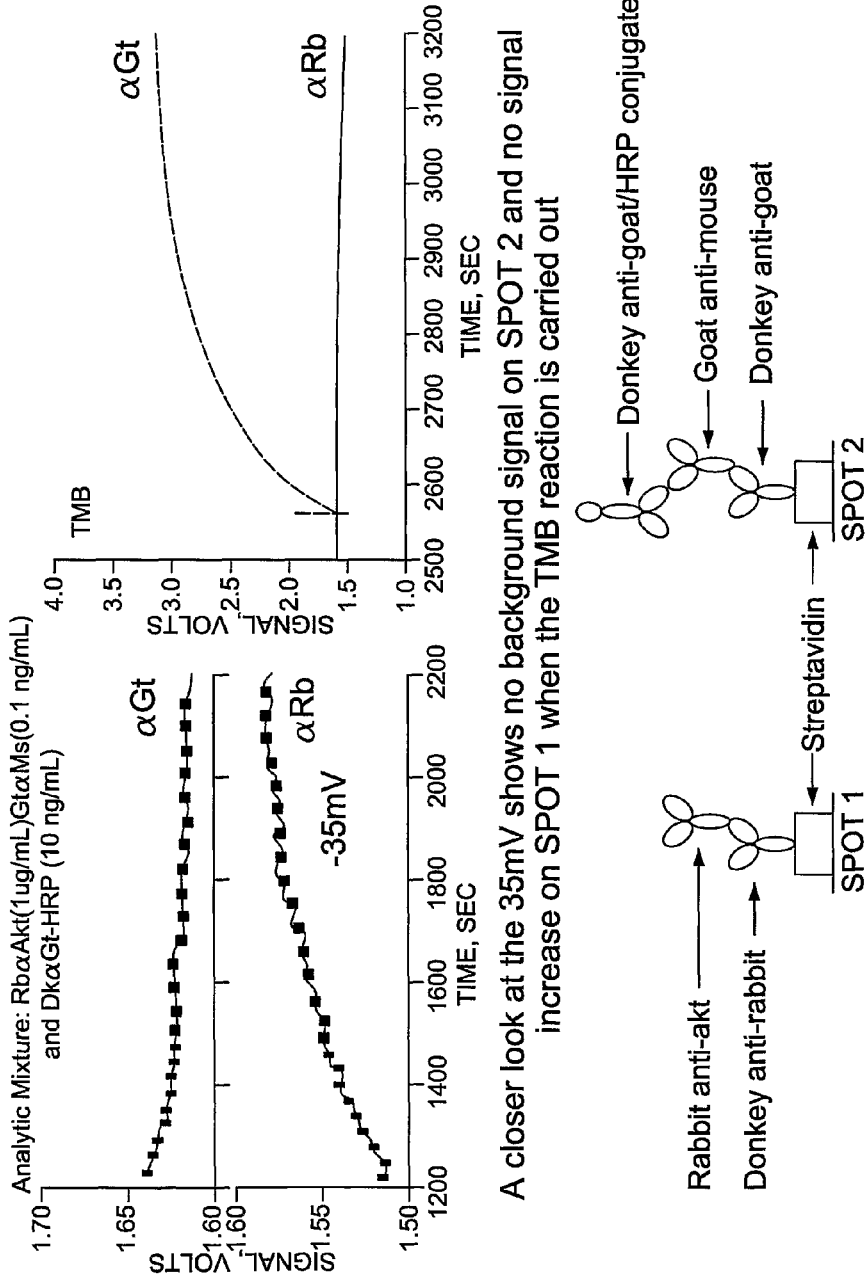
FIG. 5 shows a close-up view of the direct binding and TMB precipitation (indirect detection) shown in FIG. 4. The 35 mV signal shows no background interference on SPOT 2 and no signal increase on SPOT 1 when the TMB reaction is carried out.

The A,B,C mixture was introduced into the system: one can observe the binding event on SPOT1 (red trace) in FIG. 4, a close-up view of this graph is shown in FIG. 5.

Figure 6:
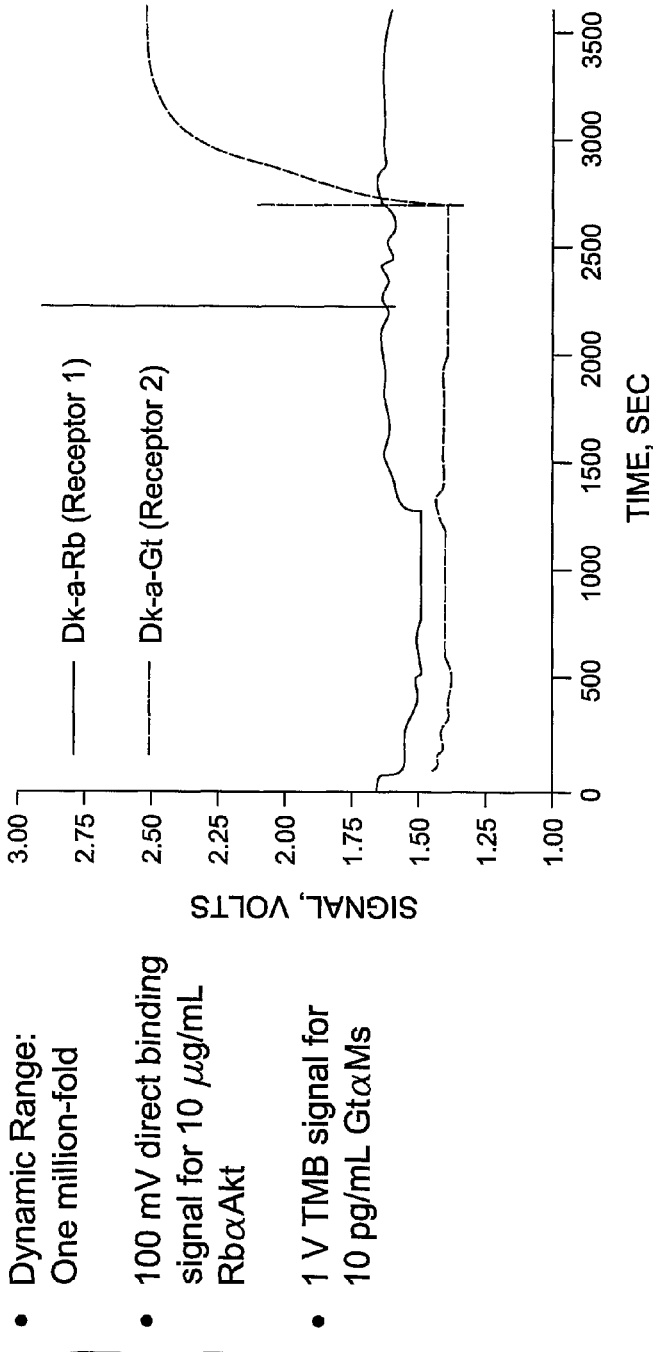
FIG. 6 shows the detection of two analytes binding over a 1,000,000-fold-concentration range. The signals (in volts) induced by the dynamic range assay shown in FIG. 3 of Rabbit anti-Akt (Rbα.Akt) (10 µg/mL) and Goat anti-mouse (Gtα.Ms) (10 pg/mL) binding to their substrates are shown as a function of time (in seconds).
Figure 7:
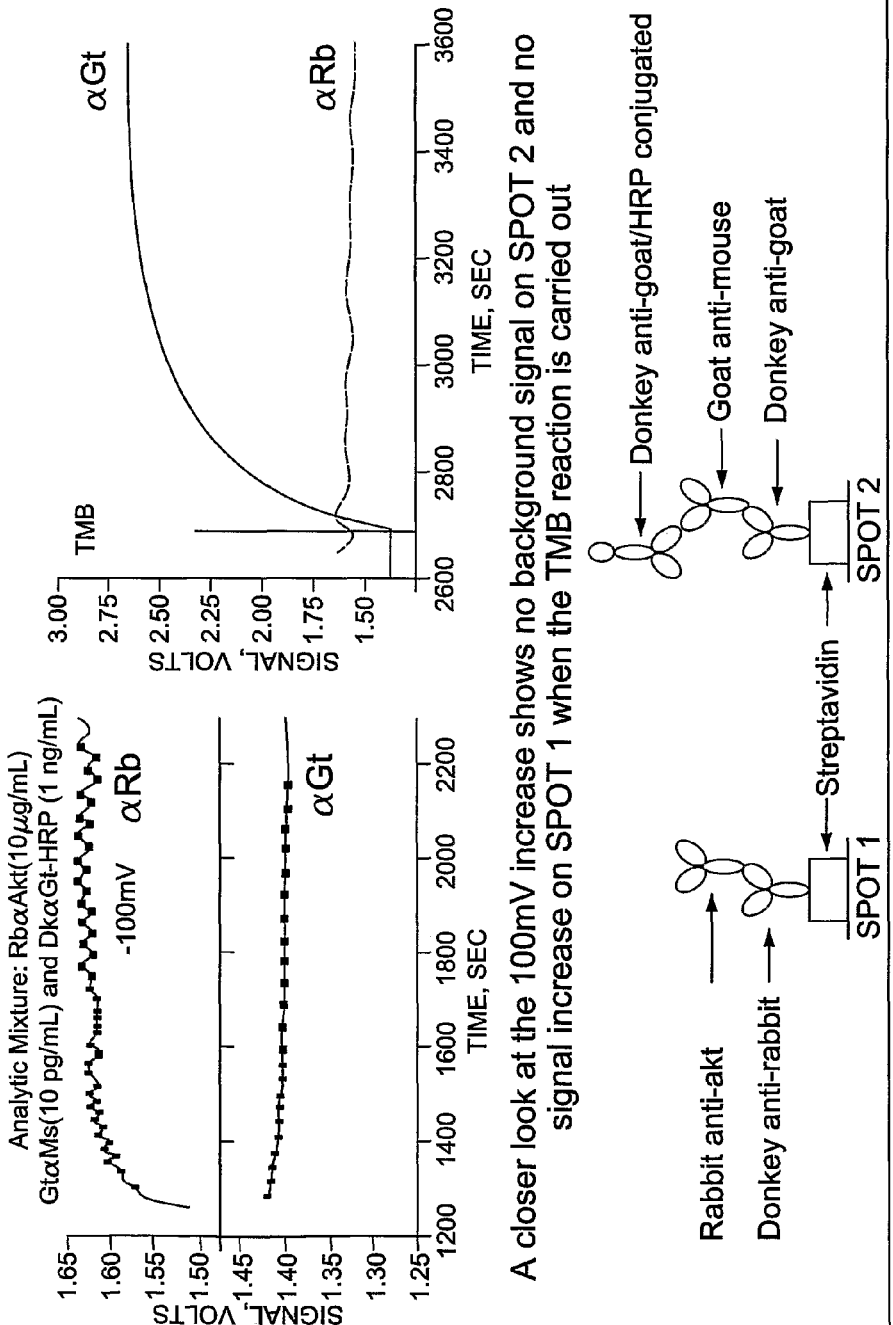
FIG. 7 shows a close-up view of the direct binding and TMB precipitation (indirect binding) portrayed in FIG. 6. The 100 mV increase shows no background interference on SPOT 2 and no signal increase on SPOT 1 when the TMB reaction is carried out.

The left panel of FIG. 5 shows a closer look at the TMB precipitation mediated by the HRP conjugated antibody immobilized on SPOT2. In both cases, the signal is specific to the immobilized species, hence no direct binding is detectable on SPOT2 and only upon addition of TMB is there a large signal. Finally, no increase in signal is seen on SPOT1 as expected upon addition of TMB. This experiment was repeated with a 10 fold lower concentration of the SPOT2 analyte and a 10 fold higher concentration of the SPOT 1 analyte. Both analytes are easily detected in the same sample as evidenced by FIGS. 6 and 7.

Example 2

Figure 9:
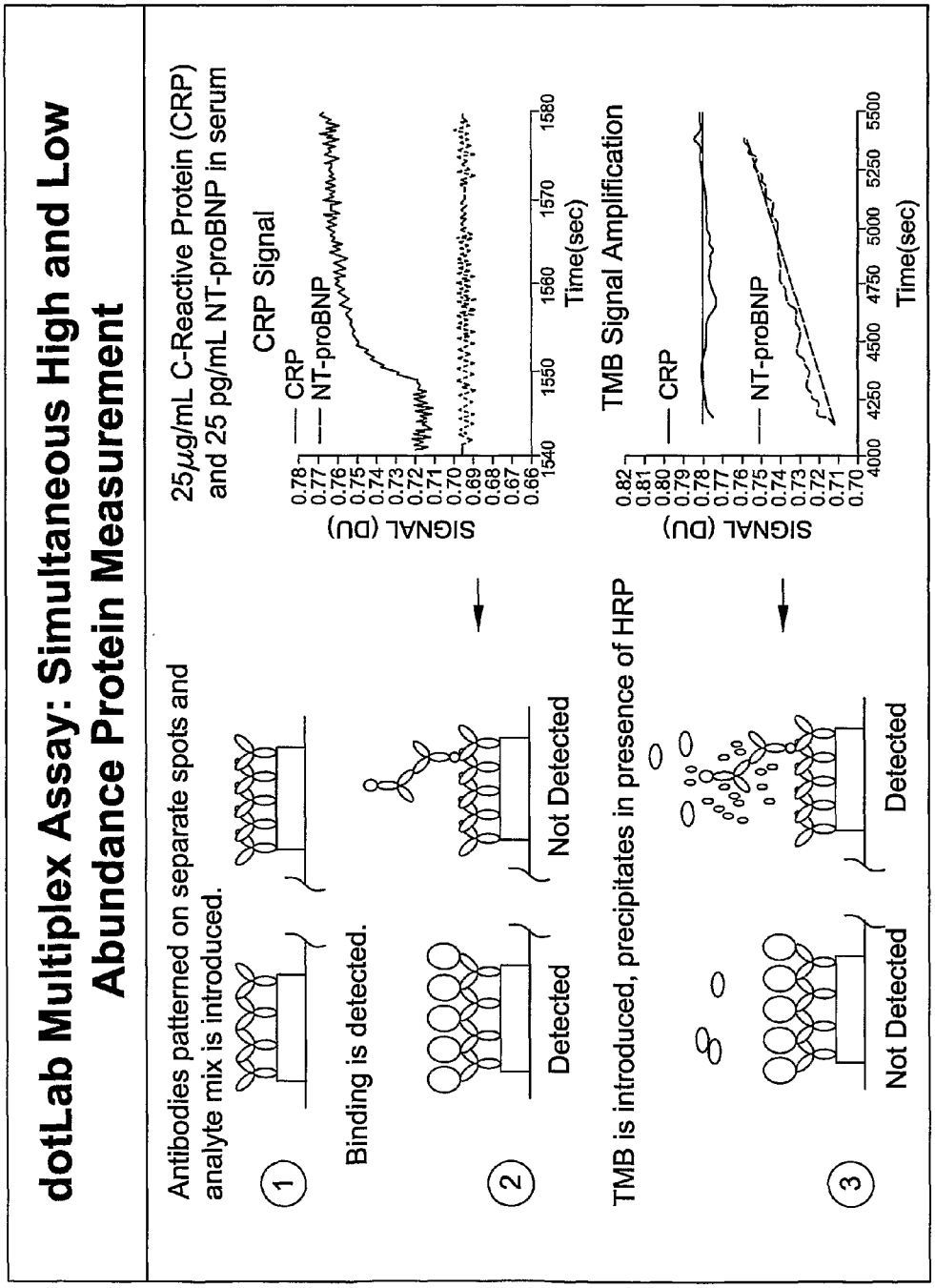
FIG. 9 is a schematic depiction of the binding of CRP and NT-proBNP to a device of the invention. Binding of CRP is measured directly (upper graph), while binding of NT-proBNP is measure indirectly (lower graph). The detection of one analyte does not interfere with the detection of the other.

In this example, antibodies for CRP and NT-proBNP are coupled to two separate spots in a single sensor. When a serum sample is introduced, CRP is detected directly at micromolar concentrations. After a brief wash, the NT-proBNP is detected at picomolar levels through the addition of a signal enhancing reagent. The unique properties of this detection method means there is no observed cross-talk between analytes, a common limitation of multiplexed endpoint assay approaches (FIG. 9).

Figure 10:
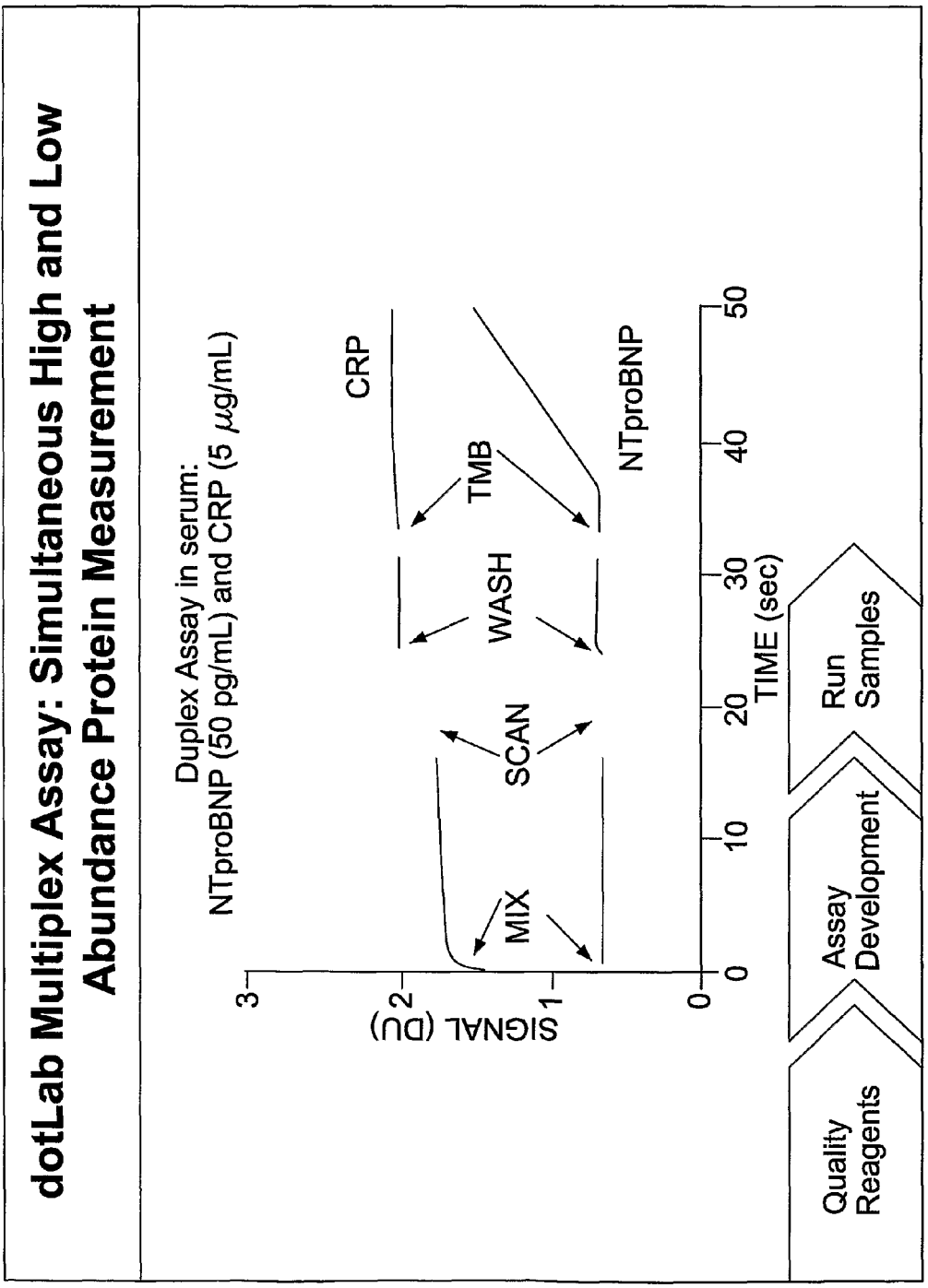
FIG. 10 is a graph of the detection of CRP and NT-proBNP, where the sample was pre-incubated with anti-NT-proBNP conjugate to HRP. The binding of CRP was detected directly, while the binding of NT-proBNP was detected after TMB was added.

To improve assay throughput, reagents can be premixed with the sample and incubated offline. Here a 60 µl serum sample was incubated for 40 minutes with the HRP coupled anti-NT proBNP secondary antibody (5% by volume) and then introduced into the sensor. The sensor has anti-CRP coupled to one detection spot and anti-NT proBNP on an adjacent spot (FIG. 10).

Figure 11:
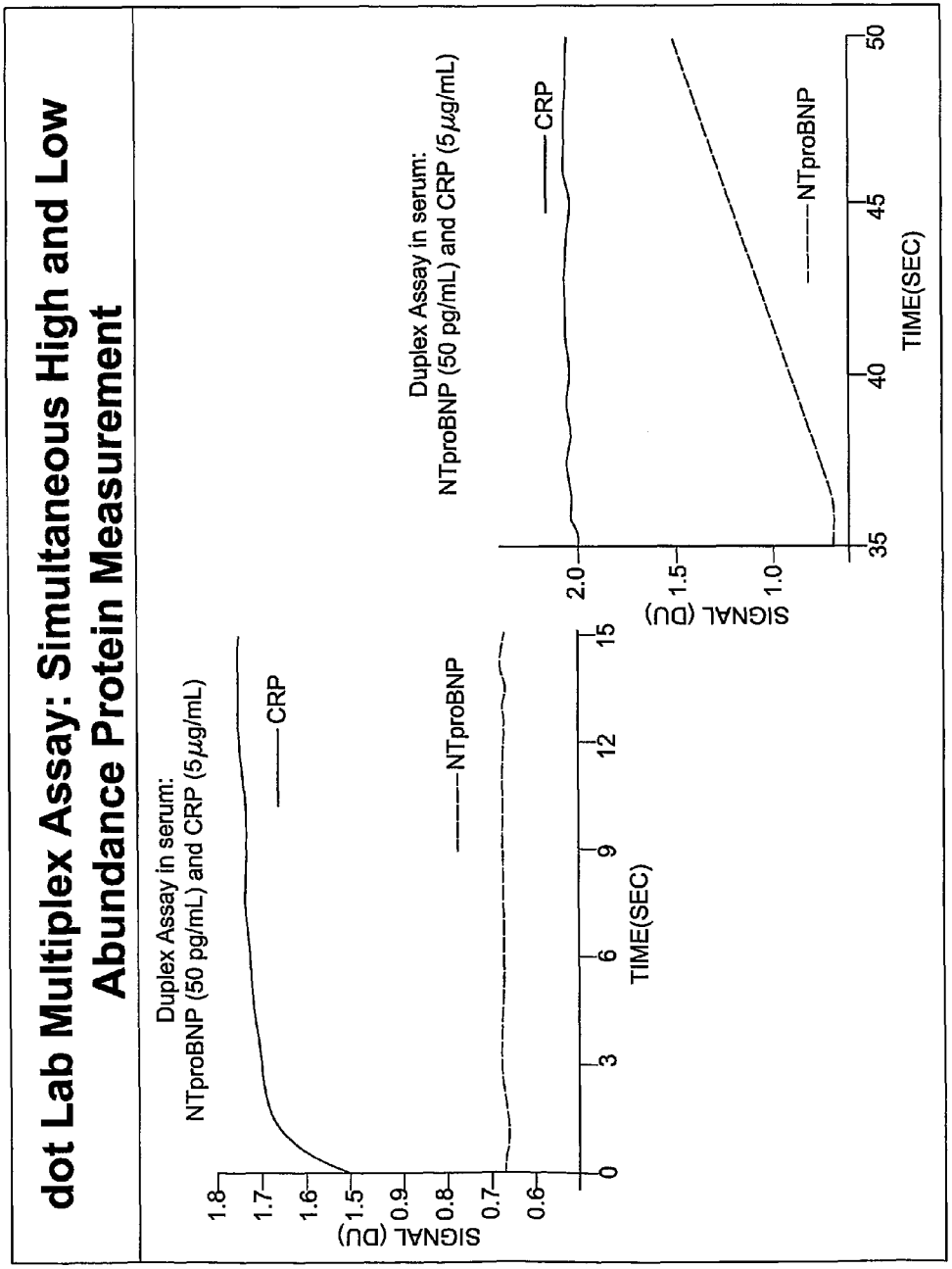
FIG. 11 is a series of graphs showing the direct detection of CRP and the indirect detection of NT-proBNP from the same sample. Detection of CRP does not interfere with detection of NT-proBNP and vice versa.

An immediate binding curve was observed for the CRP due to its concentration of 5 µg/ml. No direct signal was observed on the NT proBNP spot due to its 5 log lower concentration of 50 pg/ml. However an immediate rate curve was detected upon addition of the precipitating TMB reagent that was used for quantification. No crosstalk was observed between the two analytes in spite of the wide concentration differences and the entire detection stage of the assay was complete in 60 sec (FIG. 11).

Other embodiments are in the claims.

What is claimed is:

1. A method of detecting analytes in a sample in parallel, wherein the concentration of a first analyte is at least 100 times greater than the concentration of a second analyte, said method comprising:
   a). contacting said sample with a device having a first immobilized binding agent to which said first analyte specifically binds and a second immobilized binding agent to which said second analyte specifically binds, wherein each of said binding agents is disposed in a pattern capable of optical diffraction when said first or second analyte binds thereto; and
   b). measuring in parallel the binding of the first and second analytes to the first and second immobilized binding agents by the optical diffraction from each of said patterns to detect the presence or absence of the first and second analytes, wherein the binding of the first analyte is measured directly and the binding of the second analyte is indirectly measured using an additional moiety to amplify the optical diffraction.

2. The method of claim 1, further comprising determining the concentration of said first or second analyte in said sample.

3. The method of claim 1, further comprising calculating the rate of binding of said first or second analyte to said first or second binding agent.

4. The method of claim 1, further comprising calculating a binding constant of said first or second analyte to said first or second binding agent.

5. The method of claim 1, wherein said first or second analyte comprises DNA.

6. The method of claim 1, wherein said first or second analyte comprises RNA.

7. The method of claim 1, wherein said first or second analyte comprises protein.

8. The method of claim 1, wherein said first or second analyte comprises lipid.

9. The method of claim 1, wherein said first or second analyte is a virion.

10. The method of claim 1, wherein said first or second analyte is a cell.

11. The method of claim 1, wherein said additional moiety is horseradish peroxidase.

12. The method of claim 1, wherein said additional moiety is a bead.

13. The method of claim 1, wherein said additional moiety is alkaline phosphatase.

14. The method of claim 1, wherein said concentration of said first analyte is at least 1,000 times greater than said concentration of said second analyte.

15. The method of claim 1, wherein said concentration of said first analyte is at least 10,000 times greater than said concentration of said second analyte.

16. The method of claim 1, wherein said concentration of said first analyte is at least 100,000 times greater than said concentration of said second analyte.

17. The method of claim 1, wherein said concentration of said first analyte is at least 1,000,000 times greater than said concentration of said second analyte.

18. The method of claim 1, wherein said concentration of said first analyte is at least 10,000,000 times greater than said concentration of said second analyte.

19. The method of claim 1, wherein said concentration of said first analyte is at least 100,000,000 times greater than said concentration of said second analyte.

20. The method of claim 1, wherein said concentration of said first analyte is at least 1,000,000,000 times greater than said concentration of said second analyte.

21. The method of claim 1, wherein said concentration of said first or second analyte in said sample is less than 100 milligrams/milliliter.

22. The method of claim 1, wherein said concentration of said first or second analyte in said sample is less than 10 milligrams/milliliter.

23. The method of claim 1, wherein said concentration of said first or second analyte in said sample is less than 1 milligram/milliliter.

24. The method of claim 1, wherein said concentration of said first or second analyte in said sample is less than 100 micrograms/milliliter.

25. The method of claim 1, wherein said concentration of said first or second analyte in said sample is less than 10 micrograms/milliliter.

26. The method of claim 1, wherein said concentration of said first or second analyte in said sample is less than 1 microgram/milliliter.

27. The method of claim 1, wherein said concentration of said first or second analyte in said sample is less than 100 nanograms/milliliter.

28. The method of claim 1, wherein said concentration of said first or second analyte in said sample is less than 10 nanograms/milliliter.

29. The method of claim 1, wherein said concentration of said first or second analyte in said sample is less than 1 nanogram/milliliter.

30. The method of claim 1, wherein said concentration of said first or second analyte in said sample is less than 100 picograms/milliliter.

31. The method of claim 1, wherein said concentration of said first or second analyte in said sample is less than 10 picograms/milliliter.

32. The method of claim 1, wherein said concentration of said first or second analyte in said sample is less than 1 picogram/milliliter.

33. The method of claim 1, wherein said first or second binding agent comprises protein.

34. The method of claim 33, wherein said protein is an antibody.

35. The method of claim 1, wherein said first or second binding agent is a polynucleotide.

36. The method of claim 1, wherein said first or second binding agent is immobilized via a biotin avidin or biotin streptavidin interaction.

37. The method of claim 1, wherein said first or second binding agent is immobilized on said device via Protein G.

38. The method of claim 1, wherein at least one said binding agent is an antibody which is immobilized on said device via Goat Anti-Mouse-Fc (GAM-Fc).

39. The method of claim 1, wherein at least one of said first or second binding agent is immobilized on said device via an amide bond.

40. The method of claim 1, wherein said device comprises a third binding agent that selectively binds a third analyte and measures the binding of said third analyte.

41. The method of claim 40, wherein said device comprises a fourth binding agent that selectively binds a fourth analyte and measures the binding of said fourth analyte.

42. The method of claim 1, wherein said first or second analyte is C-peptide.

43. The method of claim 1, wherein said first or second analyte is glycated hemoglobin.

44. The method of claim 1, wherein said first or second analyte is a lipoprotein.

45. The method of claim 44, wherein said first or second analyte is a low-density lipoprotein (LDL).

46. The method of claim 44, wherein said first or second analyte is a high-density lipoprotein (HDL).

47. The method of claim 1, wherein said first or second analyte is a cytokine.

48. The method of claim 47, wherein said first or second analyte is IL-6.

49. The method of claim 1, wherein said first or second analyte is TSH.

50. The method of claim 1, wherein said first or second analyte is anti-TPO antibody.

51. The method of claim 1, wherein said first or second analyte is a hormone.

52. The method of claim 1, wherein said first or second analyte is C-reactive protein.

53. The method of claim 1, wherein said first or second analyte is gelsolin.

54. The method of claim 1, wherein said first or second analyte is copeptin.

55. The method of claim 1, wherein said first or second analyte is NT-proBNP.

* * * * *